United States Patent [19]

Takara

[11] Patent Number: 5,267,568
[45] Date of Patent: Dec. 7, 1993

[54] STRESS LEVEL MEASURING DEVICE

[76] Inventor: Atsunori Takara, No. 2306-616 Takeyama Danchi, 2-3-10 Takeyama, Midori-Ku, Yokohama-shi, Japan

[21] Appl. No.: 765,763

[22] Filed: Sep. 26, 1991

[30] Foreign Application Priority Data

Nov. 16, 1990 [JP] Japan .................. 2-308692

[51] Int. Cl.⁵ ............................... A61B 5/02
[52] U.S. Cl. ................... 128/687; 128/702; 128/704
[58] Field of Search ............... 128/689, 687, 703, 706, 128/707, 702, 704; 364/413.03, 413.05; 73/865.1

[56] References Cited

U.S. PATENT DOCUMENTS

| | | | |
|---|---|---|---|
| 3,837,333 | 9/1974 | Bruckheim | 128/706 |
| 4,232,682 | 11/1980 | Ueth | 364/413.03 |
| 4,281,663 | 8/1981 | Pringle | 128/689 |
| 4,347,851 | 9/1982 | Jundonsan | 364/413.03 |
| 4,417,306 | 11/1983 | Citron et al. | 364/413.03 |
| 4,499,904 | 2/1985 | Sidorenko et al. | 128/703 |
| 4,606,352 | 8/1986 | Geddes et al. | 128/702 |
| 4,729,381 | 3/1988 | Harada et al. | 364/413.03 |
| 4,790,326 | 12/1988 | Mather et al. | 128/689 |
| 4,803,625 | 2/1989 | Fu et al. | 364/413.03 |
| 4,807,639 | 2/1989 | Shimizu et al. | 128/706 |
| 4,858,125 | 8/1989 | Washizuka et al. | 364/413.03 |
| 4,938,228 | 7/1990 | Righter et al. | 128/706 |
| 4,958,641 | 9/1990 | Digby et al. | 128/702 |
| 5,056,527 | 10/1991 | Go et al. | 128/702 |
| 5,058,597 | 10/1991 | Onada et al. | 128/704 |

FOREIGN PATENT DOCUMENTS 1209634 9/1986 Japan .
62-53633 3/1987 Japan .
64-49538 2/1989 Japan .

*Primary Examiner*—Randall L. Green
*Assistant Examiner*—Bob Clarke
*Attorney, Agent, or Firm*—Browdy and Neimark

[57] ABSTRACT

A stress level measuring instrument compares a base-line pulse value with other pulse values of the subject. The instrument includes a device for calculating the mean pulse frequency, a device for determining the basic pulse frequency, a device for comparing the basic pulse frequency and the base-line pulse frequency, a device for calculating the stress level, and a display.

3 Claims, 6 Drawing Sheets

| 10 / 15 | 06:30 | 12 |
|---|---|---|
| ELAPSED TIME | 08 | 13 |
| PULSATION | ⌣ | 14 |
| PRESENT VALUE | 51.5 | 15 |
| LOWEST VALUE | 51.1 | 16 |
| BASIC VALUE | 50.3 | 17 |

STRESS LEVEL MEASURING DEVICE

FIELD OF INVENTION

This invention relates to a stress level measuring instrument which measures the lowest beating value of heart (pulse frequency, often referred to as the "pulse") with an electronic measuring instrument for comparison with past data to enable judgment of the degree of physical exhaustion and mental stress on the day of measurement.

BACKGROUND OF THE INVENTION

Remarkable progress has been made in recent medical appliances by virtue of the development of electronic technology, and there are various instruments used for diagnosis of diseases and health.

The pulsimeter is one of the instruments used for such a purpose, and there are many prior proposals related to pulsimeters. The pulse frequency generally varies every moment, and a method for accurate measurement of pulse frequency over a short time is the crux of the problems with pulsimeters. For this purpose, cycle conversion methods are generally employed in which the time of the pulse cycle of pulsation signals is measured to convert the measured value into pulse frequency per minute. This method still has a problem of data reliability due to variance in sampling data, and methods of decreasing the degree of the variance in data by comparing the variance with the reference value are proposed in the Japanese patent laid open No. 61-209634 (S. Ichikawa) and others. A method of obtaining mean values accurately and in a short amount of time by arithmetic processing of pulsation values in time sequence is proposed in the Japanese patent laid open No. 64-49538 (Y. Jikiba).

All of these prior proposals relate to the pulsimeter itself, and the general lay public with no medical knowledge finds it extremely difficult to judge health conditions directly using the measured values.

An instrument for measuring the degree of improvement in physical strength obtained by exercising is therefore proposed in the Japanese patent laid open No. 62-53633 (H. Fujii), wherein a device is added to a pulsimeter which measures the time required for recovery to the normal pulse frequency after exercise by pre-setting the normal pulse frequency of the user in the pulsimeter. The Fujii proposal intends to measure the person's physical strength by the time required for recovery of the pulse frequency which has increased because of exercise, the object of which is different from that of the present invention which displays his health condition by comparison with the person's past historical data.

What is more, an instrument which measures the health condition by the judgment of pulse wave speed is available on the market, but it is too expensive and unsuitable for personal use.

It is difficult to measure the condition of health of humans and display it precisely. This is so because no appropriate criteria are available up to the present which can precisely represent the health condition of people, and the only appropriate way is collective judgment by specialists from body temperature, pulse electrocardiogram, etc.

SUMMARY OF INVENTION

It is, accordingly, an object of the invention to overcome deficiencies of the prior art, such as those mentioned above.

It is another object of the present invention to provide a stress level measuring instrument, which can measure physical exhaustion and mental stress, i.e. the stress level by a simple method, and can analyze and evaluate the result.

It is a further object of the present invention to provide a stress level measuring instrument for use both at hospitals and homes which enables use of a simple method for the judgment of a person's physical condition with no requirement for particular expert knowledge.

It is still another object of the present invention to provide a stress level measuring instrument which is light in weight, easy to manipulate, easy to carry, and low in the cost.

The present inventor obtained knowledge from experience to the effect that the lowest value of the pulse frequency, i.e. fluctuation in the pulse frequency while lying quiet, can be a gauge which represents the health condition of humans. He has, according to the present invention, developed a measurement/display instrument which can precisely display the health condition of humans using an electronic measuring instrument based on that knowledge.

That knowledge is supplemented with the following explanations.

(A) Range of fluctuation in bodily temperature and pulse frequency:

When a patient enters any hospital, it is standard operating procedure to measure his temperature and pulse several times a day. The measurement is extremely important for learning the physical condition of the patient, particularly the state of any disease the patient may have.

The body temperature varies in the range from 36 degrees Celsius to as much as about 42 degrees Celsius. The ratio of the variation is $42 \div 36 = 1.17$, namely, with 17% variance between the standard value and the maximum value.

On the other hand, the pulse frequency can be up to the maximum of 200, with 70 as the standard value. The ratio of the variance is expressed by $200 \div 70 = 2.85$ when calculated in the similar way. The increase in the maximum value can be as large as 185%. This means the variance is 10 times compared with that of the body temperature.

While the time constant of change in the body temperature is said to be about 6 minutes, pulsation change can take place in about 3 seconds. The reaction rate of the latter is 100 times higher than that of the former.

As a result of studying the characteristics of violently varying pulses, there has now been devised a detecting and displaying method of pulse frequency correlated with health condition, with the ability of detecting such delicate change which a thermometer can not detect. The extreme difference of pulse frequencies indicates that minor change in the condition of a patient can be sensed.

(B) Relationship between "stress level" and degree of health:

Stress is a function of the defense mechanism in humans against external stimulation. It is a disease when stress exceeds a certain limit. The condition of health becomes worse with an increase in stress.

The pulse frequency varies sensitively in accordance with posture, i.e. standing, sitting or lying, and constantly repeats fluctuation even in the stand-still state with a constant posture. When the load on the body increases, the pulse frequency immediately increases. It is common experience that the pulse frequency increases accordingly when a person walks, runs or lifts something.

This fact shows that the organ controlling the pulse frequency receives load conditions from various parts of the body and reacts to these. It can be easily estimated that the pulse frequency will become lower with the decrease in loads including a case of recovery from diseases. The frequency is least in the lying posture. The principle is utilized to judge the health condition of humans.

(C) Relationship between "stress level" and basic pulse frequency:

In general, the lower the pulse frequency, the better the physical condition of the person in question. In fact, it is said that the pulse frequencies of marathon runners are considerably less than those of people who do not exercise. Proper exercise continued for a long time is considered to gradually decrease the pulse frequency in proportion to the improvement in the degree of health.

As a result of continuously measuring normal pulse frequencies from the beginning of a light jogging exercise of 2 kilometers at a time, it was confirmed that the action of the pulse decreased by an average one beat per minute every day for the period of 2 weeks. This observation is evidence confirming that pulsation reacts sensitively in accordance with unconscious minor changes of the body.

If one starts jogging at the same time every day and the pulse frequency at the time of starting is measured, it can be seen that the value differs every time. It is thus indicated that the pulse frequency is closely related to physical condition. The pulse frequency at the time of starting varies in accordance with the conditions immediately before the pulse is measured. The pulse frequency is high immediately after activity, such as at the time of coming home from an outing, and low after a nap. It has been made clear that the pulse frequency is fairly dependent on daily conditions. For instance, the lowest pulse frequency can be measured if the pulse frequency is measured every morning immediately upon awakening, in bed, when one is in the most relaxed state, in the same way as women measure the basal body temperatures for contraception. Moreover, when the conditions for the measurements are identical, one can ensure more accurate measurements. The pulse frequency at the time when one is most relaxed yields the lowest value. The lowest value of the pulse frequency is hereinafter referred to as "basic pulse frequency."

This basic pulse frequency, however, naturally varies depending on the season and the physical condition of the person. Therefore, basic pulse frequencies of a person are measured for a long term period, and the lowest value (herein called the "lowest limit basic pulse frequency") is recorded. This lowest limit basic pulse frequency represents the best physical condition of the person. In other words, the difference between the lowest limit basic pulse frequency and the basic pulse frequency measured on the day represents the degree of poor physical condition. Therefore, the value obtained by subtracting the lowest limit basic pulse frequency from the basic pulse frequency is herein called the "stress level." The lowest limit basic pulse frequencies, however, are often renewed in the early stage of measurements. Although they are often renewed every week in the early stage, the intervals of renewal become less frequent, resulting in renewal annually or semiannually.

When this kind of state is reached, the stress level represents the person's physical conditions very precisely.

The foregoing objects are accomplished in the stress level measuring instrument of this invention by providing:

(a) means for calculating a mean pulse frequency wherein a mean pulse frequency per unit time is calculated continuously from a cycle time of a unit of pulse signals detected by a pulse detector, and the thus obtained value of the mean pulse frequency is stored temporarily in a memory and/or displayed one by one, (b) means for determining a basic pulse frequency wherein the value of mean pulse frequency obtained by said means for calculating a mean pulse frequency is compared with the value of succeeding mean pulse frequency, a resulting lowest value of mean pulse frequency is stored temporarily in a memory as the lowest mean pulse frequency, said lowest mean pulse frequency is renewed every time a new lowest value thereof appears, then the last obtained lowest of mean pulse frequency is decided to be the basic pulse frequency processed on the day, and said basic pulse frequency is stored in the memory and/or displayed, (c) means for renewing the lowest limit basic pulse frequency wherein the basic pulse frequency obtained by said means for deciding a basic pulse frequency is compared with the lowest limit value of the same person's basic pulse frequency measured in the past, said lowest limit value is renewed when a basic pulse frequency measured on the day which is less than the lowest limit value of the basic pulse frequency measured in the past appears, and the renewed lowest limit value is stored and/or displayed, (d) means for calculating a stress level wherein the value obtained by subtracting the lowest limit value of the same person's basic pulse frequency measured in the past from the basic pulse frequency processed on the day is stored as the stress level, and (e) means for displaying a stress level wherein the stress level obtained by said means for calculating a stress level is displayed with a series of the same person's stress levels measured in the past predetermined period.

BRIEF DESCRIPTION OF DRAWINGS

The above and other objects and the nature and advantages of the present invention will be more apparent from the following detailed description taken in conjunction with the drawing wherein:

FIGS. 4, 5, 6-1 and 6-2 are block diagrams illustrating features of the invention.

DETAILED DESCRIPTION OF INVENTION

Figure 1:
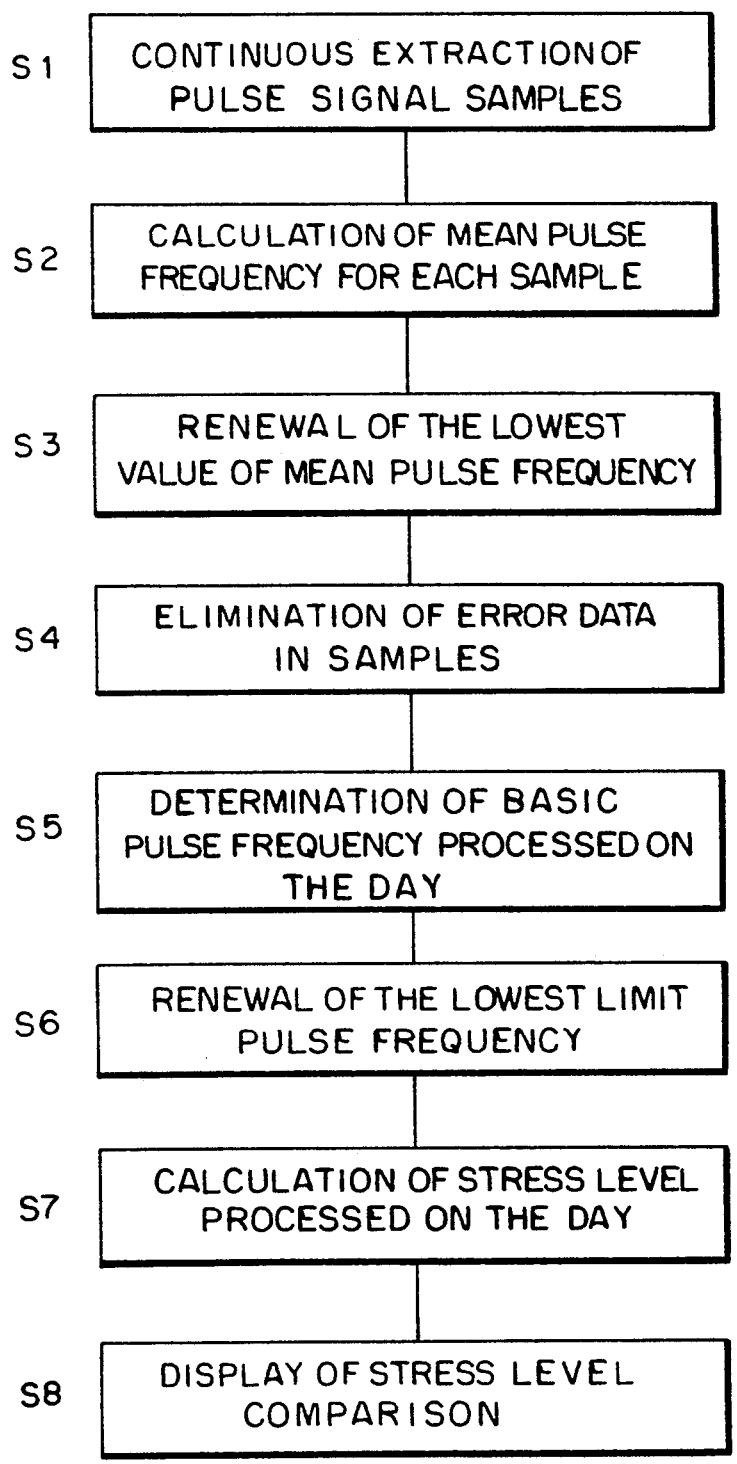
FIG. 1 is a flow chart showing the principle of the invention, which is explained hereinafter in more detail.

To start with, samples of pulse signals are continuously extracted in step S1.

In general, each sample is extracted in a unit of from 5 to 10 pulses, and the sample is subjected to batch processing for the calculation of the mean pulse frequency.

Mean pulse frequency is calculated for each sample in step S2.

The reason why the mean pulse frequency is employed is that the variance is great if the cycle time of pulse is measured with the unit of 1 to 2 pulses, and the mean value is calculated by batch processing the pulse signals of at least 5 or more pulses.

The cycle time for each unit of pulse signals is measured herein with 6 beats of pulse frequency for the calculation of the mean pulse frequency per unit time (e.g. 1 minute).

The cycle time is measured by counting a number of pulses of the clock pulse corresponding to the pulse signals of extracted 6 beats, i.e. the length of wave. When 100 hertz is employed for the clock pulse, the time can be measured with as small a unit as 1/100 second.

Then the pulse frequency per unit time (1 min.) is calculated back using the measured cycle time. The significant digits of the obtained mean pulse frequency are counted with the accuracy of 0.1 beat because the measurement is made with the unit of 1/100 second.

The lowest value of the mean pulse frequency processed on the day is recorded for renewal in step S3.

This process comprises successive comparison of the measured mean pulse frequency for each sample and recording of the lowest value. Experimentally, the lowest value of this processing time gradually converges in 5 to 10 minutes, and a value lower than that will not be obtained even if measured for longer time. An approximately 8 minute measurement is sufficient.

Error data in the sample are removed in step S4 (to be described later).

The lowest value of the mean pulse frequencies obtained in step S5, from which those caused by error data are removed, is determined to be the basic pulse frequency of the day's processing, recorded, and displayed on a screen or other device. In step S6, the basic pulse frequency of the day's processing is compared with the lowest limit value of the person's basic pulse frequency (lowest limit basic pulse frequency) measured in the past, and the lowest limit basic pulse frequency is renewed and displayed on a screen or other device if the basic pulse frequency of the day's processing is lower than the lowest limit basic pulse frequency.

The stress level of the day's processing is obtained in step S7.

This stress level can be obtained by subtracting the lowest limit basic pulse frequency measured in the past from the basic pulse frequency processed on the day.

The stress level processed of a given day is displayed in comparison with the stress level of the person during a certain period in the past. For this purpose, stress level for a certain period of at least 2 weeks must be stored. For the display of comparison, the date of the graph is automatically advanced when a switch is pressed to instruct the end of measurement, and the stress level during a certain period, 2 weeks for example, including the day of measurement is shown on a display or other device in a graphic form.

Removal of Error Data

Sneezing or an occurrence of an irregular pulse during pulse measurement causes a big change in the value of pulse frequency. Particularly in the case of irregular pulse, the interval between pulses becomes longer which results in a longer counting time for the unit pulse frequency (6 beats), and the mean pulse frequency calculated based on the time gives a comparatively small value. Therefore, means to remove those error data is provided in the stress level measuring instrument for the removal of error data caused by an irregular pulse or other reasons.

If a mean pulse frequency appears which is lower than the lowest pulse frequency stored temporarily by the time of measurement in step S3 of FIG. 1, the difference from the last lowest pulse frequency is calculated in Step S4, and the mean pulse frequency is deleted as error data caused by an irregular pulse of another reason if the difference is larger than a certain threshold value.

By means of suggestion, normal fluctuation in the mean pulse frequency is about 1 to 2 beats, but that caused by irregular pulse is as many as 3 to 4 beats. Therefore, "3" is adopted as the threshold value E experimentally, and fluctuations of the lowest pulse frequency which exceed 3 or more beats are removed as error data caused by irregular pulse or other reason.

Generation of Signal Tone For Lowest Pulse Frequency Renewal

As mentioned above, the lowest pulse frequency is frequently renewed immediately after the beginning of measurement, but after several minutes it seldomly renews. The stress level measuring instrument displays the value of the lowest pulse frequency at the time of its renewal in step S3, and at the same time arouses attention of the user by giving a signal tone.

By this provision, the user is not obliged to watch the instrument always, easily recognizing that the basic pulse frequency of the day is reached because the interval between signal tones becomes longer and finally the tone is not heard any more.

Functions

According to the aforementioned stress level measuring instrument, pulse frequency is measured by time. There are many such gauges for measuring physical conditions of human beings such as the blood pressure, bodily temperature, etc., and pressure and temperature must be measured for the measurement of the parameters. According to the latest technology, however, measurement of these parameters gives better accuracy than those of pressure and temperature, and the pulse frequency is selected as the basis for the stress level measurement. What is more, accurate measurement with no variance can be achieved because the mean pulse frequency per unit time is employed for the measurement of the pulse frequency.

Next, the pulse frequency at the time of the person's best condition of the day is recorded as the basic pulse frequency by extracting the lowest value of this mean pulse frequency.

In addition, the reliability is improved by removing error data at this time caused by an irregular pulse and other reasons.

Then, the basic pulse frequency of the day is compared with the lowest limit value of the the person's basic pulse frequency measured in the past, the lowest limit value is renewed by the basic pulse frequency which is less than the value when it appears, and the person's lowest value, namely the basic value representing the best condition, is constantly renewed to improve the reliability of the data.

The lowest limit basic pulse frequency in the past is subtracted from the basic pulse frequency on the day to represent the stress level by the difference, eliminating individual differences and enabling magnified display of the degree of changes. Direct display with the basic pulse frequency requires wider range of graduation for a graphic display because the individual differences in basic pulse frequency are large, resulting in smaller graphic display.

The fluctuation of the individual differences can be limited within a certain range if the difference between the basic pulse frequency and the lowest limit basic pulse frequency is employed for representation. In addition, the degree of the fluctuation can be enlarged in the display which uses absolute values of pulse frequency (usually about 70 beats per minute) because the difference between the basic pulse frequency and the lowest limit basic pulse frequency is normally about 10 to 20 beats per minute.

On the other hand, the fluctuation of the mean pulse frequency in a day is about 1 to 2 beats, and the mean pulse frequency must be measured with the accuracy of 1/10 beat to detect minor changes.

Final display of the thus obtained stress level in comparison with the past data can show the person's physical and health conditions very clearly.

Detailed Embodiment

An embodiment of the stress level measuring instrument is explained as disclosed in the drawings.

Figures 2, 3:
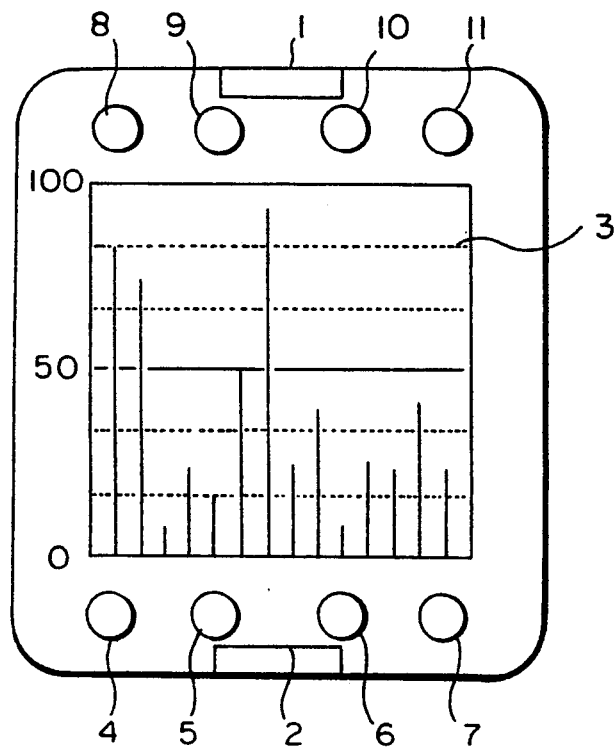
FIG. 2 is the plain figure of the stress level measuring instrument designed for portable use.
FIG. 3 is an example of a liquid display which might be displayed on the instrument of FIG. 2.

FIG. 2 is the external appearance of the stress level measuring instrument designed for portable use, and FIG. 3 is an embodiment of the display for the stress level measuring instrument shown in FIG. 2.

The instrument is provided with fixing portions 1 and 2 for a band which is fixed for wearing the instrument around the arm. Therefore, the pulse can be measured while traveling, by carrying this instrument on the arm. A liquid crystal display 3 provided with several different modes gives different displays by mode switching. For example, mode 1 displays a graph of stress data during a period of about two weeks. Mode displays time of measurement; elapsed time; condition of pulsation; present and the lowest values of the measured pulse; and the lowest limit basic pulse value.

FIG. 2 illustrates a graphic display of the stress level data for two weeks which is given by mode 1. The X axis shows dates of measurement with the capacity of 14 days. The Y axis shows stress levels, which are the values obtained by subtracting the lowest limit basic pulse frequency from the basic pulse and multiplying the result by a constant (e.g. 5).

The base of the graph, i.e. stress level "0" is a reference value corresponding to the lowest limit basic pulse frequency. The center solid line shows the border line between healthy and semi-healthy conditions which is divided into 3 zones, and the upper region of semi-healthy condition is also divided into 3 to show respective levels.

Four switches each, totaling eight, are provided on the upper and lower sides of the display. Switches 4, 5, and 6 are respectively the power ON switch, initiation of measurement switch, and stop switch for terminating measurement. Switches 7, 8, 9, and 10 are, respectively, the switches for power OFF; correction of calendar clock; selection for year, month, date, and hour; and data modification. Switch 11 is a switch for changing the display mode.

FIG. 3 is a liquid crystal display 3 showing an example of mode 2.

A display area 12 for the time and date of measurement displays the date of measurement as well as the time of measurement in hours and minutes. A display area 13 for elapsed time is displayed in minutes. A display area 14 for pulsation condition, is displayed with a heart shape flashing for the inspection of the wearing condition of the pulse detector. A display area 15 for the current pulse frequency displays the pulse frequency currently being measured. A display area 16 is provided for the lowest pulse frequency, and the lowest value of the measured value of the pulse on the day is represented by the number of beats. A display area 17 is provided for the lowest limit basic pulse frequency, and the lowest basic pulse frequency measured in the past is shown by the number of beats.

Figure 4:
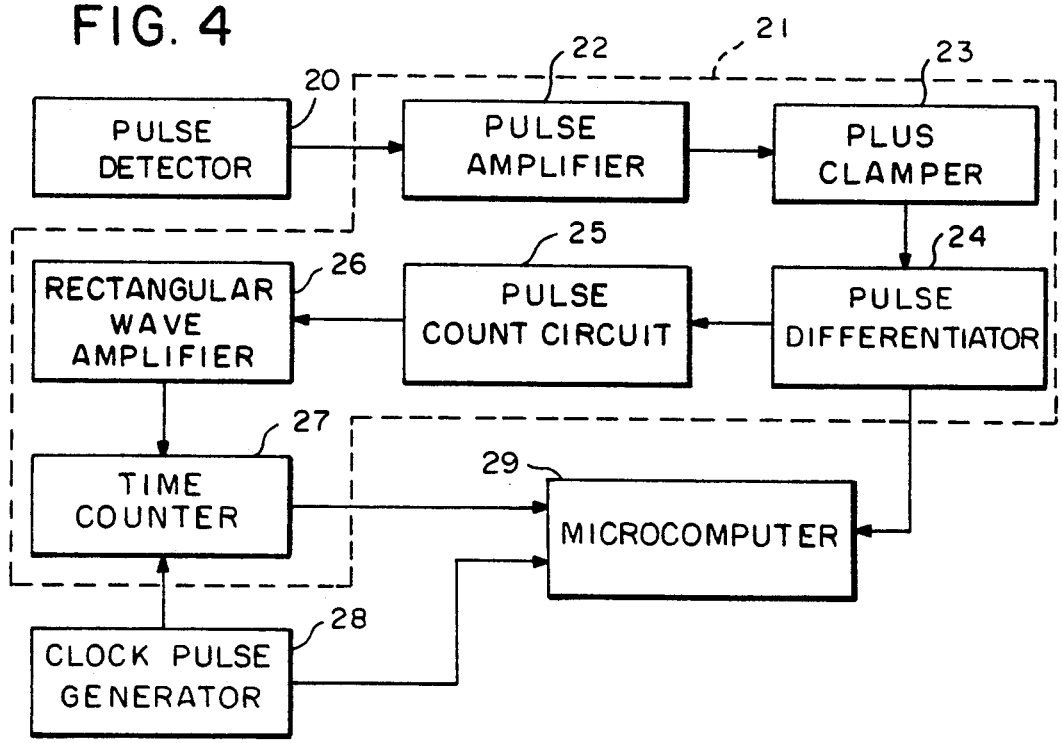

FIG. 4 is a block diagram showing the configuration of this invention. In the diagram, 20 is a pulse detector whose light-interceptor detects changes caused by pulsating flow which is created by the light applied to a finger tip, and produces waveforms corresponding to the pulse frequency.

A pulse counter 21 is provided for computing the mean pulse frequency by the pulse waveforms detected by the pulse detector 20, comprising a pulse amplifier 22, pulse clamper 23, pulse differentiator 24, pulse count circuit 25, rectangular wave amplifier 26, and time counter 27.

Pulse amplifier 22 comprises a circuit to amplify the pulse waveforms detected by pulse detector 20, pulse clamper 23 is a circuit to reshape the pulses of pulsation by cutting the noise level, and pulse differentiator 25 differentiates the pulses of pulsation to sharpen the rising of pulses. These pulses working with the pulsation are sent to microcomputer 29 to be processed for displaying. The display is made in the pulse condition display area 15 in FIG. 3, and is used to inspect the wearing condition of the instrument. Pulse count circuit 25 is a bucket circuit for counting the pulses sent by a unit of pulse frequency, for instance 6 beats, charging the capacitor stepwisely every time a pulse is input, and discharging by the voltage detecting diode when the voltage reaches a predetermined level. Precise stepwise waveforms corresponding to 6 beats of pulse are thus formed.

The rectangular wave amplifier 26 is a circuit which reshapes the stepwise waveforms obtained by the pulse count circuit 25 to adjust the amplification level. The time counter 27 is a circuit for the measurement of the length of rectangular wave corresponding to 6 beats of pulse, namely the time, and produces appropriate pulses by dividing the clock pulse sent from the clock pulse generator 28 to obtain the count proportionate to the length of the rectangular waves. If the clock pulse is structured with 100 hertz pulse, the time corresponding to 6 beats of pulse can be expressed by a numerical value with the unit of one hundredth of a second. Pulse frequency per minute, i.e. mean pulse frequency, can be obtained if the number of count, i.e. time, for 6 beats obtained by the time counter 27 is calculated back by the microcomputer 29.

Figure 5:
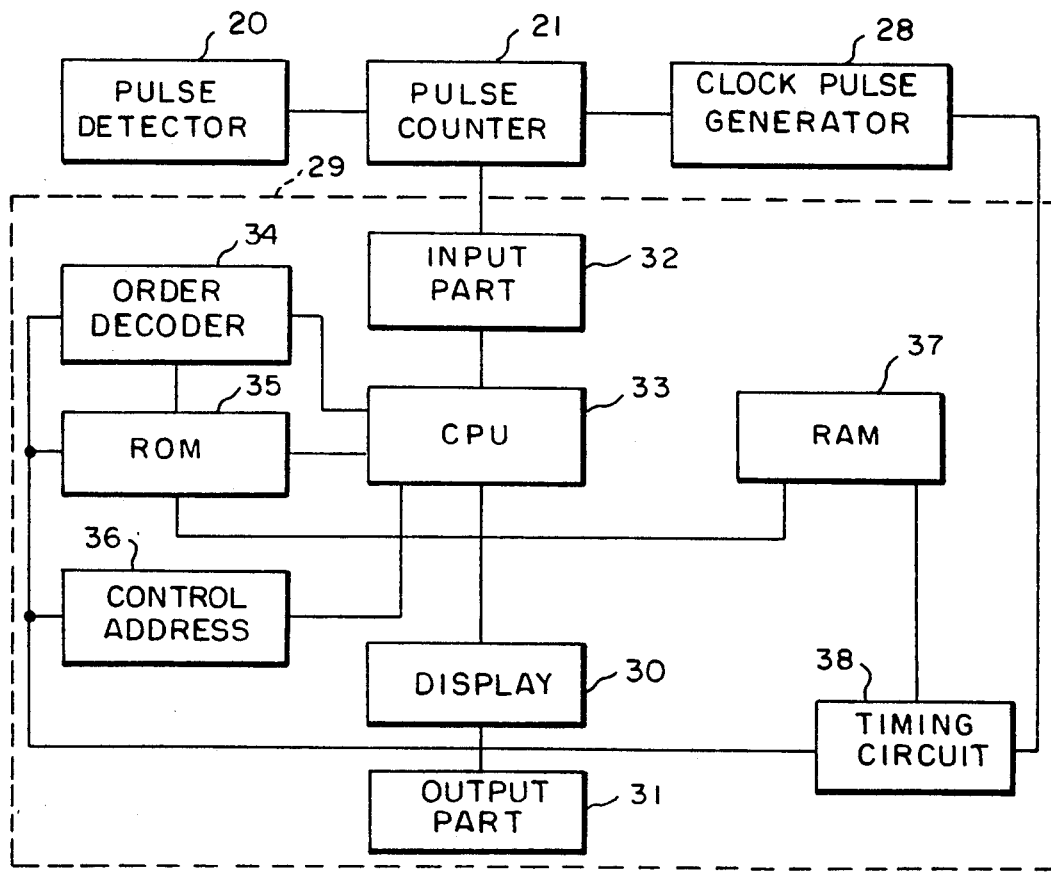

FIG. 5 is a more detailed block diagram of the microcomputer 29 shown in FIG. 4. Display is at 30, and output part is at 31. An input part 32 is provided to send the pulse frequency obtained by the pulse counter to CPU 33 for arithmetic processing.

An order decoder 31 decodes instructions for transfer, search, computation, output, input, etc. by the instructions from the timing circuit to control the CPU.

A ROM 35 is provided where the program which controls this system is stored.

A control address 36 specifies the addresses of data in ROM, RAM, etc.

A RAM 37 is provided in which the result of arithmetic calculation and other data are temporarily stored.

A timing circuit 38 produces various timing signals from the clock signals given by the clock pulse generator to supply to ROM and others.

The function of the stress level measuring instrument structured as above are explained with reference to FIGS. 2, 3, 4 and 5.

In connection with this embodied example, explanation is made with the unit pulse frequency of 6 beats, time counter frequency of 100 hertz, and threshold value for removing irregular pulse of 3 beats.

When the pulse detector 1 is worn, with the finger tip applied with detecting light, the light interceptor detects changes in pulsating flow, and waveforms corresponding to pulse frequencies are produces. The pulse waveforms are input to the pulse counter 21 and amplified by the pulse amplifier 22. Noise level waveforms are cut by the pulse clamper 23, and reshaped as pulses by the pulsation.

The purpose of the series of circuits is a preprocessing to make the values of fluctuating pulse wave heights uniform, to remove weak pulses appearing irregularly, and to measure the resulting pulse frequency with the accuracy of down to 0.1 beat. Beat by beat measurement of pulsation is impractical because of the large variance, and 6 beats is used as a unit to calculate the mean value. For this purpose, the pulses of pulsation reshaped by the pulse clamper 23 are processed by the pulse count circuit 25 with 6 beats as a unit to be converted to stepwise waveforms.

Next, the waveforms are converted to accurate rectangular waves by the rectangular wave amplifier 26, and sent to the time counter 27. Counts proportionate to the length of the rectangular wave are obtained here by the rectangular wave corresponding to 6 beats of pulse and 100 hertz pulses. The number of the count represents the time corresponding to 6 beats of pulsation expressed by numerical values with the unit of 1/100 second.

The values are sent to the input part 32 of the microcomputer 29.

The measured pulse frequencies are processed by the microcomputer 29 for the calculation of the mean pulse frequency; removal of irregular pulses; renewal and registration of the lowest mean pulse frequency; calculation of the stress level; display of stress level comparison; and renewal and registration of the lowest limit basic pulse frequency; etc.

Figures 1, 6:
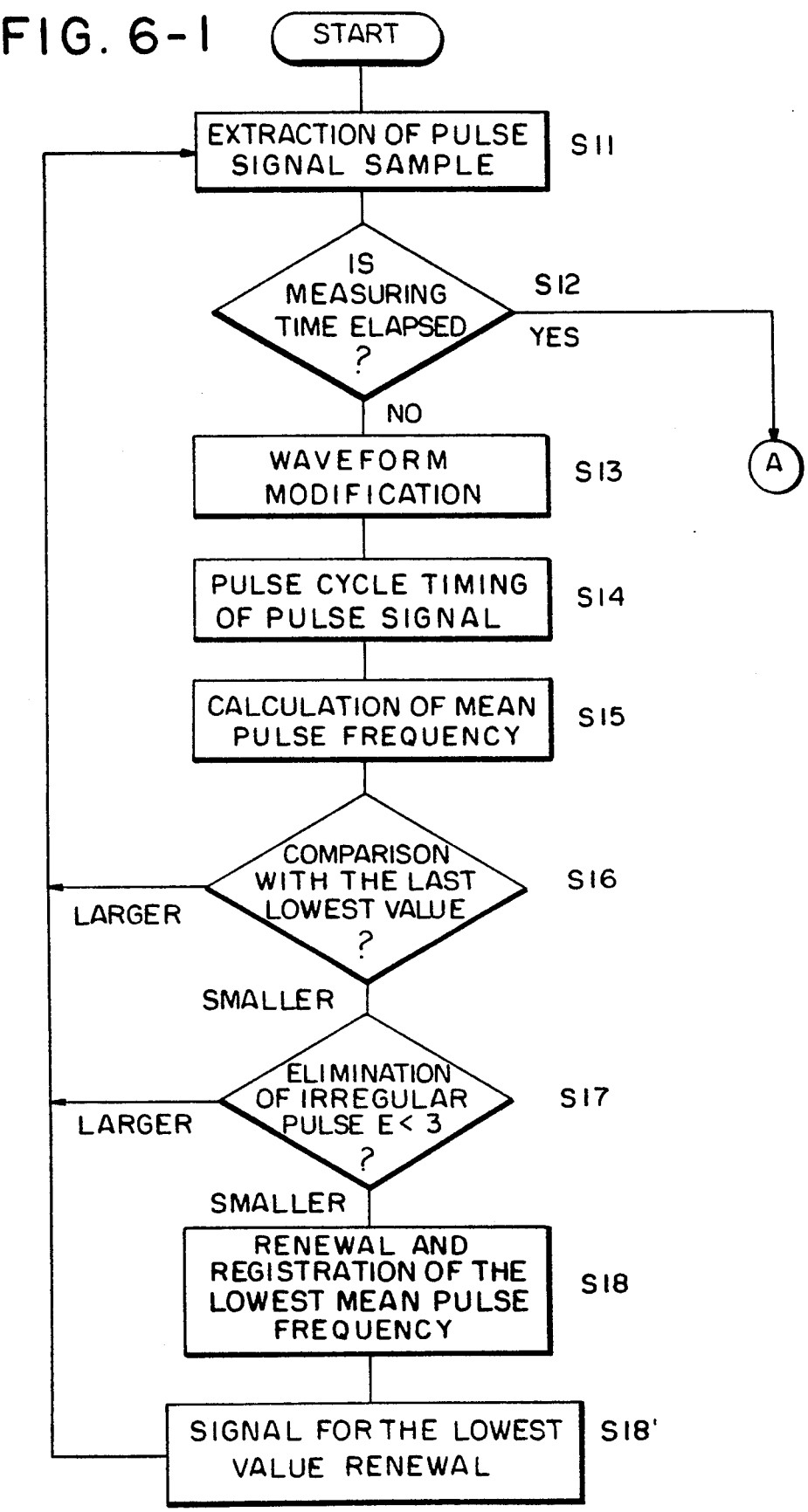
Figures 2, 6:
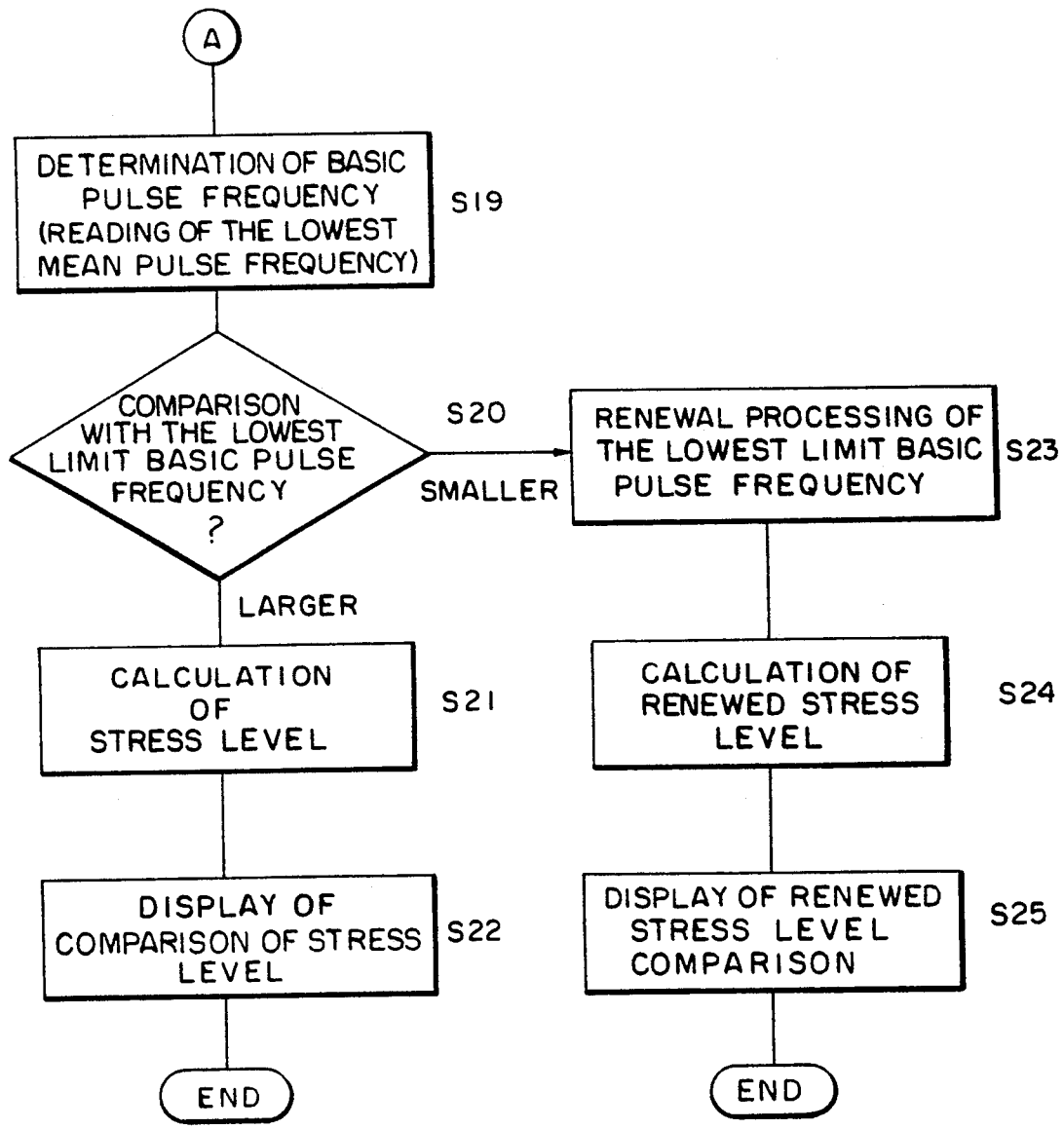

These processes are explained with reference to the flow chart given in FIG. 6.

A samples of pulse signal is extracted by the pulse detector 20 in the step S11. The step S12 checks whether the measurement is made within the measuring time. The measurement time can be optionally set by the user for 2, 5, or 8 minutes.

If it is less than the set time, a series of processes from the pulse amplifier 22 to the rectangular wave amplifier 26 are carried out to form a rectangular wave of 6 beats.

The 6 beat rectangular wave is counted by the 100 hertz pulses obtained by the division of pulses from the clock pulse generator 28 to measure the length of the rectangular wave, i.e. time with the unit of 1/100 second.

In step S15, pulse frequency per minute M (mean pulse frequency) is calculated from the number of count T obtained in step S14 using the following equation:

Time for one beat (minute/beat):

$$t = T \times 1/100 \times 1/60 \times 1/6 = T/36,000$$

Mean pulse frequency (beats/minute):
$M = 1/t = 36000/T$.

The mean pulse frequency is compared with the last lowest value of the mean pulse number in step S16. If the value is larger than the last lowest value, the process is returned to S11 to extract the next sample. If the value is lower than the last lowest value, the processing proceeds to step S17 to remove error data caused by irregular pulses and other reasons.

At this stage, a value lower than the lowest value up to the last time and exceeding the threshold value is treated as error data and removed.

If the measurement of pulse is made using the mean value of 6 beats as mentioned above, normal changes in mean pulse frequency per minute are mild, increasing or decreasing only by 1 to 2 beats. However, if irregular pulse if contained in the 6 beats, the mean value can change by as much as 3 to 4 beats which can be easily noticed. Therefore, if "3" is employed as the comparing condition for the comparator, those with less than 3 beat increase or decrease are allowed to pass and sent to the next step S18. Those with rapid changes with 3 or more beats are judged to have been caused by irregular pulse or other reason, and eliminated to prevent them from being transferred to the following circuit.

In step S18, the mean pulse frequencies of samples sent in succession are compared one by one, and renewal and registration is made if there is one which is lower than the past lowest value.

Pulse frequency continues to increase and decrease several times in a few minutes. When it increases to reach a certain value, it starts decreasing, and then turns to increase again from a low value, fluctuating constantly. This low value level is cut down many times during the measurement. The value ceases to decrease in an almost certain period of time. The time is experimentally about 8 minutes.

Sometimes it is difficult in the morning to constantly watch the instrument because of sleepiness. To solve the problem, a signal tone is given to arouse the user together with the displayed information every time the lowest pulse frequency is renewed in step S18 during measurement. The user can learn the measurement condition without watching the instrument.

When 8 minutes pass, Step S12 measures the elapsed time of measurement and the processing jumps to Step S19.

Basic pulse frequency is determined in step S19. The lowest value of the mean pulse frequency finally obtained in step S12 is taken in as the basic pulse frequency, which is stored in the memory. In step S20, the basic pulse frequency obtained in step S19 is compared with the lowest value of the person's basic pulse frequency (lowest limit basic pulse frequency) measured in the past.

If the basic pulse frequency processed that day is larger than the lowest limit basic pulse frequency, the process proceeds to the next step S21.

Stress level is computed in step S21. The stress level is a value obtained by subtracting the lowest limit basic pulse frequency from the basic pulse frequency processed on the day, and is multiplied by 5 times for greater convenience in displaying. In step S22, the stress level measured on the day is compared with the stress level measured in the past and displayed. This is performed in mode 1 as shown in FIG. 2, and the stress level measured on the day is displayed together with the stress level for the past 2 weeks in the form of bar chart on the liquid display 3. If the basic pulse frequency processed on the day in step 20 is less than the lowest limit basic pulse frequency, the process proceeds to S23 to renew and register the lowest limit basic pulse frequency.

As a result, calculation and display of comparison are made basing on the lowest limit basic pulse frequency renewed in steps S24 and 25.

In addition, the lowest limit basic pulse frequency is displayed in the lowest limit basic pulse frequency area 17 with flashing when it is renewed to inform the user of the renewal.

Although the embodied example of this invention is based on a case where the pulse frequency is measured by a pulsimeter, similar results can be obtained when the time intervals of pulses are directly measured. The method is basically the same when a heart beat meter or electrocardiograph is used.

Use of the Instrument

Power source is set on when the power ON switch 4 shown in FIG. 2 is pressed, and the mode 1 graph appears on the liquid crystal display. This shows the stress level for the past 2 weeks. When the display mode change switch 11 is pressed, the mode 2 is activated to display the measured data. Pressing the measurement start switch 5 activates the pulse detector 20 to measure the pulse. The time of measurement can be optionally set to 2, 5, 8 or any length of minutes. The current values during measurement vary every moment, and the values are displayed in the display area 15 on the display shown in FIG. 3. Every time the lowest value is renewed, the value is displayed in the display area 16 and a signal tone is heard, informing the user of the renewal of the lowest value without looking at the display.

When the preset measuring time has passed, the value of the elapsed time is displayed stationarily in the elapse time display area 13 and a signal tone of buzzer or other is given. Then, pressing the measurement termination switch 6 changes the displayed image automatically to advance the date of the graph, and a graph which shows the stress level for 2 weeks including the day of the measurement is displayed.

In addition, when the lowest limit basic pulse frequency is renewed, the value is displayed by flashing in the display area 17 together with a graph of the stress level produced based on the renewed standard value.

When the measurement is completed, the power OFF switch 7 is pressed to shut off the power.

Experimental Example

The result of an actual use of the stress level measuring instrument of this invention if introduced.

Figure 7:
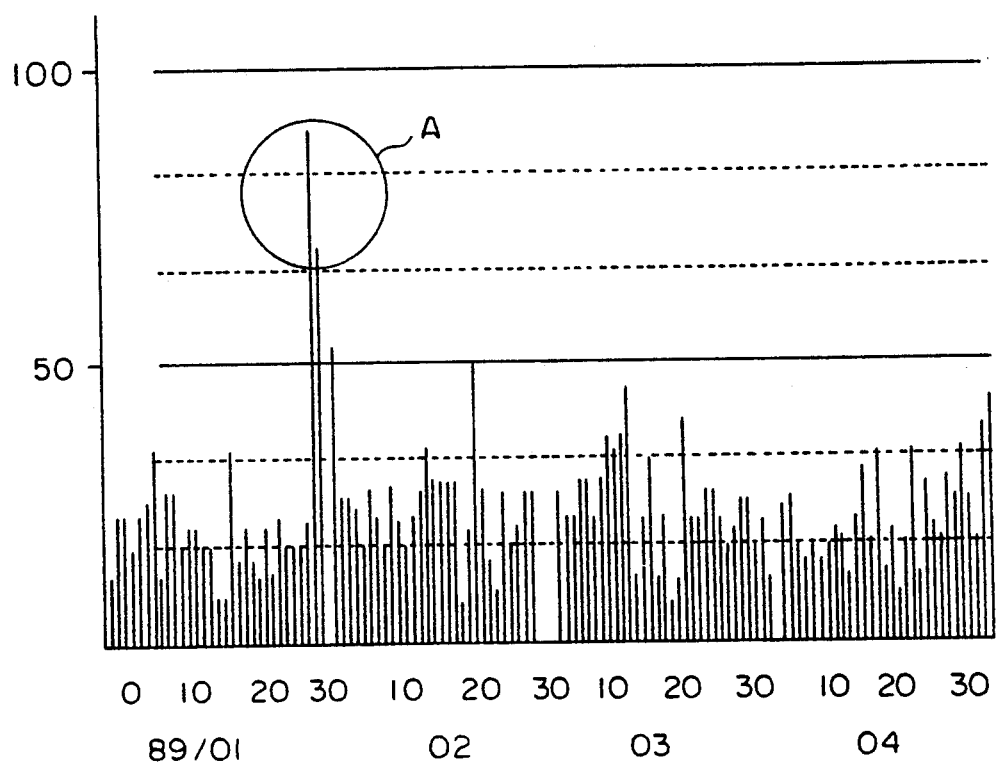
FIGS. 7 and 8 are graphs showing results of use of an instrument according to the present invention.

FIG. 7 is a graph showing the result of an 8 minute measurement every morning immediately after rising for 4 months from January to April, 1989.

As seen from the graph, one can say that the physical condition is good because the stress levels during the period were below 50 which indicate a generally healthy condition. The level, however, rapidly jumped up at point A at the end of January. When the measurement was made, the subject had little subjective symptoms while the values of measurement rapidly jumped up, and it was suspected that something was wrong with the instrument. Measurements were carried out again after 1 hour and after 2 hours with no change in the measured values, which indicated that he was in unsatisfactory physical condition. It was found later that he had had a slight cold at the time of measurement. He went to hospital for 2 days and had a rest. He regained his health in 4 days.

Figure 8:
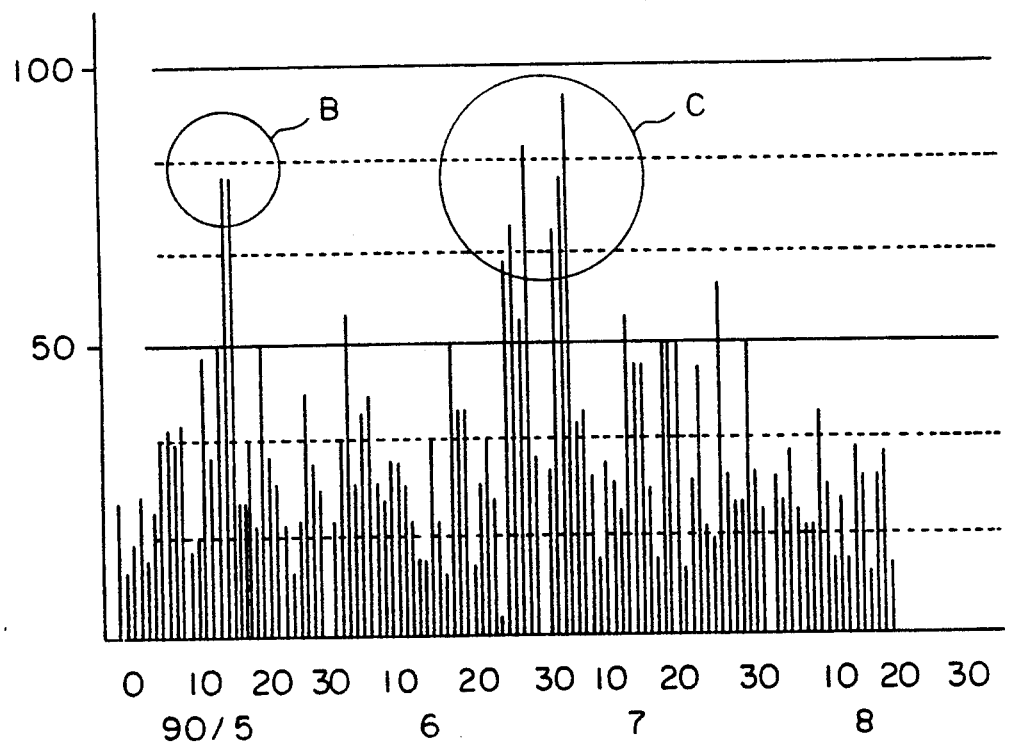

FIG. 8 is the record from May to the middle of August, 1990.

Abnormal values B and C are observed in the middle of May and in the period from the end of June to the beginning of July. At the time of B, the subject caught cold and had a two day rest to get well again. At the time of C, he caught cold again. He went to hospital for diagnosis, but he was too busy to take a rest, making the cold worse. The result is well displayed on the graph.

Comparison of FIG. 7 with FIG. 8 indicates that FIG. 7 has lower pulses with less variance. This represents seasonal variance. Low values appear in March and April on the average when the climate is mild, and higher values generally appear in gloomy climate like in the rainy season and when the temperature varies violently.

Effects of the Invention

A person's physical condition can be accurately displayed by the use of this stress level measuring instrument. In addition, with a longer period of usage of the data, the standard value of a person's basic pulse frequency, i.e. (the lowest limit) basic pulse frequency approaches the actual value to enable measurement of accurate stress level. Individual differences can be eliminated because this stress level is the difference between his basic pulse frequency measured on the day and his lowest limit basic pulse frequency measured in the past.

The instrument is extremely effective for the measurement of delicate change in the physical condition because the pulse frequency which is the basis for the stress level can be measured with 1/100 second accuracy by the use of 100 hertz pulses, which gives accurate mean pulse frequency up to 0.1 beat.

The degree of the variance can be enlarged for display by comparing the stress level with the difference between thus obtained mean pulse frequency and the lowest limit basic pulse frequency. The variance of the pulse can be clearly displayed graphically by multiplying the stress level by an appropriate constant for enlarged display.

As the result, unnoticeable light colds and accumulated state of stress can be clearly detected on a graph, and even lay people having no special medical knowledge can easily judge their physical conditions by utilizing the instrument for the health care.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A stress level measuring instrument comprising:
    (a) first calculating means for continuously calculating a mean pulse frequency per unit time from a cycle time of a unit of pulse signals detected by a pulse detector,
    (b) second means for deciding a basic pulse frequency wherein a value of said mean pulse frequency obtained by said first calculating means is compared with a succeeding value of said mean pulse frequency, a lower value of said means pulse frequency being stored temporarily in a memory as a tentative lowest value of said mean pulse frequency, said tentative lowest value of said mean pulse frequency being replaced every time a new lower value of said mean pulse frequency appears, said tentative lowest value of said mean pulse frequency being finally determined to be a basic pulse frequency measured for a day,
    (c) third means for replacing a lowest limit value of said basic pulse frequency wherein a value of said basic pulse frequency obtained by said second means is compared with a lowest limit value of said basic pulse frequency measured over a long term period before said day of determining said basic pulse frequency of said day, said lowest limit value being replaced when a value of said basic pulse frequency measured for said day is less than said lowest limit value of said basic pulse frequency measured over said long term period,
    (d) second calculating means for calculating a stress level wherein a value obtained by subtracting said lowest limit value of said basic pulse frequency measured over said long term period from a value of said basic pulse frequency measured for said day is stored as said stress level, and
    (e) fourth means for displaying a stress level wherein said stress level obtained by said second calculating means is displayed with a series of stress levels measured in a past predetermined period.

2. The stress level measuring instrument claimed in claim 1, further comprising:
    fifth means for removing error data wherein a new value of said mean pulse frequency is rejected as an error data when said new value of said mean pulse frequency is less than said tentative lowest value of said mean pulse frequency stored temporarily in said memory and a difference between said new value and said tentative lowest value is larger than a predetermined threshold value.

3. The stress level measuring instrument claimed in claim 1, further comprising:
    sixth means for sounding an alarm on an appearance of replacement data wherein a tone informing a subject of replacement of said lowest mean pulse frequency whenever said tentative lowest value of said mean pulse frequency stored temporarily is replaced when a new tentative lower value of said mean pulse frequency is inputted.

* * * * *